United States Patent [19]

Delcour

[11] Patent Number: 4,647,379
[45] Date of Patent: Mar. 3, 1987

[54] NITROGEN-CONTAINING WATER-SOLUBLE POLYMER FLOCCULANTS

[75] Inventor: Kees Delcour, Hoeck, Netherlands

[73] Assignee: The Dow Chemical Company, Midland, Mich.

[21] Appl. No.: 797,571

[22] Filed: Nov. 13, 1985

[51] Int. Cl.[4] .......................... B01D 21/01; C02F 1/56; C08G 73/06
[52] U.S. Cl. ..................................... 210/736; 524/800; 524/922; 528/405
[58] Field of Search ................ 528/405; 524/800, 922; 210/736

[56] References Cited

U.S. PATENT DOCUMENTS

| | | | |
|---|---|---|---|
| 3,391,090 | 7/1968 | Schiegg | 210/736 X |
| 3,523,892 | 8/1970 | Schiegg | 210/736 |
| 3,917,817 | 11/1975 | Vanlerberghe et al. | 528/405 X |
| 3,953,330 | 4/1976 | Tonkyn et al. | 210/736 X |
| 4,129,528 | 12/1978 | Petrovich et al. | 528/405 |
| 4,328,142 | 5/1982 | Hertel et al. | 523/417 |
| 4,482,667 | 11/1984 | Willis et al. | 523/400 |

*Primary Examiner*—Earl Nielsen

[57] ABSTRACT

A nitrogen-containing prepolymer is prepared by adding an epihalohydrin, particularly epichlorohydrin, to piperazine in an amount of more than one mole of epihalohydrin per mole of piperazine, in the substantial absence of strong base.

The prepolymer is reacted with polyalkylene polyamines in the absence of strong base to produce a polymeric flocculant.

16 Claims, No Drawings

NITROGEN-CONTAINING WATER-SOLUBLE POLYMER FLOCCULANTS

BACKGROUND OF THE INVENTION

This invention relates to the preparation of nitrogen-containing, water-soluble polymers prepared from polyamines and a water-soluble piperazine/epihalohydrin prepolymer, and to their use as flocculants.

The condensation of epihalohydrins with piperazine is one which has been known for many years, and which has been carried out under a wide range of varying conditions. For example, U.K. Pat. Nos. 1,448,183 and 992,011 disclose methods in which epichlorohydrin is condensed with piperazine, in the presence of strong base, for example, KOH and NaOH, to produce various insoluble solids.

Similarly, U.S. Pat. No. 2,963,483 describes a method for the preparation of N-glycidylpiperazine, and a product prepared by polymerization thereof. The N-glycidylpiperazine is prepared by treatment of piperazine with epichlorohydrin, to produce an adduct of the formula

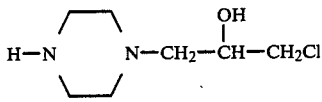

and subsequent treatment of the adduct with a base, for example sodium hydroxide, potassium hydroxide, sodium or potassium alkoxide, calcium hydroxide, or an amine base, to eliminate HCl and thereby produce N-glycidylpiperazine. The addition of epichlorohydrin, and dehydrohalogenation are carried out at a temperature of from 0° C. to 50° C., and the resulting N-glycidylpiperazine is a crystalline solid, which can be separated, and polymerized by heating to make a rubbery polymer. However, the polymerization of N-glycidylpiperazine is very difficult to control, and in practice it is difficult or impossible to stop the polymerization at a point at which the polymer is not a solid, or at best a gel.

Great Britain Pat. No. 1,416,454 purports to disclose a method for the preparation of a water-soluble polymer by condensation of epichlorohydrin and piperazine, at a mole ratio of approximately 1:1, and in the presence of strong base (NaOH). However, the reaction there disclosed is notoriously difficult to control, and almost invariably results in the production of a solid or gelled product.

European Patent Application No. 0,033,104 and corresponding U.S. Pat. No. 4,328,142 disclose the preparation of a water-soluble polymeric cross-linking agent for polyamines from epichlorohydrin and piperazine to produce a flocculant. In this method, a complex two-stage reaction is required to produce the desired water-soluble prepolymer, the first stage of which is carried out in the presence of strong base (NaOH), and the result of the first stage is then acidified, before further epichlorohydrin is added at low pH, for the second stage. Control of this reaction is difficult and therefore relatively expensive, because of the complex pH requirements. Furthermore, the overall reaction for the production of the flocculant is a three-stage one, which is complicated to implement on an industrial scale.

In view of the aforementioned deficiencies of the prior art processes, an improved method for producing water-soluble polymer flocculants which eliminates one or more of such deficiencies would be highly desirable.

SUMMARY OF THE INVENTION

The present invention is such an improved method which comprises (1) adding an epihalohydrin, for example epichlorohydrin, to piperazine, preferably in aqueous solution, in an amount of more than one mole of epihalohydrin per mole of piperazine, and polymerizing the product in the substantial absence of strong base under conditions sufficient to form a prepolymer having a relatively low molecular weight and (2) then adding the prepolymer to a polyamine in the absence of strong base, under conditions sufficient to produce a water-soluble, nitrogen-containing polymer.

Surprisingly, the practice of the method of this invention enables the production of a water-soluble polymer having the desired molecular weight.

The polymer may be utilized as a flocculant, for example, in the paper-making industry or any other industry in which flocculants are commonly utilized.

DETAILED DESCRIPTION OF ILLUSTRATIVE EMBODIMENTS

According to the invention, there is provided a method of producing a nitrogen-containing, water-soluble polymer, which method comprises a first stage of preparing a water-soluble prepolymer, by adding an epihalohydrin to a solution of piperazine in a solvent, in an amount of more than one mole of epihalohydrin per mole of piperazine, subjecting the reaction mixture in the substantial absence of strong base to conditions sufficient to produce the prepolymer and a second stage of subjecting the prepolymer to contact with a polyfunctional amine in the substantial absence of strong base under conditions sufficient to produce a water-soluble, nitrogen-containing polymer.

Both stages of the reaction in accordance with the invention are carried out in the substantial absence of strong base, i.e., bases with strengths of the order of NaOH and KOH. The presence of strong base makes both the reaction forming the prepolymer, and the subsequent reaction with the polyamine, very difficult to control, so that the desired molecular weight is obtained.

While the preferred epihalohydrin is epichlorohydrin, epibromohydrin is also suitable.

The molar ratio of the epihalohydrin to piperazine is of great importance in controlling the polymerization properties of the prepolymer. As indicated above, the epihalohydrin must be used in an amount of more than about one mole per mole of piperazine. It is preferred that the amount of epihalohydrin should be at least about 1.1 moles per mole of piperazine. If the amount of epihalohydrin is less than about 1.1 moles, the prepolymer tends to be somewhat unreactive, when reacted with the polyamine.

The upper limit of the mole ratio of epihalohydrin to piperazine is governed by practical constraints, since if substantial excess of epihalohydrin is used, for example, 2 moles per mole of piperazine, the resulting prepolymer product becomes extremely reactive in subsequent reaction with the polyamine, and thus the reaction is difficult to control, and tends to lead to gel formation. A preferred range of the starting materials is from about 1.1 and to about 1.3 moles of epihalohydrin per mole of piperazine.

Both the epihalohydrin and the piperazine are preferably utilized in the form of aqueous solutions, and the concentration of the starting materials in the aqueous solutions is preferably such to produce a concentration of the resulting prepolymer product of from about 25 to about 50 percent, preferably from about 35 to about 45 percent by weight. The concentration of the prepolymer product in the solution has a marked effect on the viscosity, and thus the ease of handling of the prepolymer product. For example, a 40 percent solution of a typical prepolymer product will have a viscosity of from about 80 to about 400 millipascals per second (mPa/s), whereas a 60 percent solution of the same product has a viscosity of about 26,000 mPa/s. The weight average molecular weight ($\overline{M}_w$) of the prepolymer is generally from about 2,000 to about 5,500.

In the preparation of the prepolymer, it is essential that the epihalohydrin be added to piperazine, not the reverse, since the reverse order of addition gives an entirely different product, which is not reactive with polyamines to produce a water-soluble polymer.

The reaction of the epihalohydrin with piperazine is exothermic, but the temperature is preferably raised initially to 50° C. or so, to allow the reaction to begin. The epihalohydrin is then added slowly and at a rate such that the reaction mixture is preferably maintained at a temperature of less than about 110° C., most preferably from about 90° C. to about 110° C. during the addition. It may be desirable to heat the reaction mixture during the later stages of the addition to maintain the temperature in this range.

The reaction mixture is preferably maintained at a temperature of from about 90° C. to about 110° C. for a further period of from 1 to 4 hours, preferably from 1 to 2 hours after the addition is complete, to complete the reaction. If the heating following the addition is carried out for a period of less than 2 hours, the prepolymer tends to be too reactive, and if for more than 6 hours, unreactive.

The prepolymer formed is believed to have a complex structure with a mole ratio of epihalohydrin to piperazine of about 1, a molecular weight, i.e., a weight average molecular weight ($\overline{M}_w$), of from about 2,000 to about 5,000, and the halogen originating from the epihalohydrin being attached to the piperazine rings in the form of HCl. The molar excess of epihalohydrin is converted to 1,3-dichloropropanol-2, which it is believed becomes attached to the polymer structure in some way.

Whatever its structure, the prepolymer can readily be polymerized with polyamines as hereinafter defined to produce water-soluble polymers again in the substantial absence of strong base. Hence, the invention should not be construed as being limited by any theory as to the structure of the prepolymer, since whatever its structure the prepolymer prepared using the particular choice of the molar ratio of starting materials, and method of prepolymerization in the absence of strong base, is water-soluble, has a high reactivity and low molecular weight, and is useful as a starting material, from which may be produced a desired water-soluble polymer, useful as a flocculant.

The reactive nitrogen-containing prepolymer is reacted with a polyamine, to produce a polymer flocculant. For the purposes of this invention, a polyamine is any organic compound having at least two amine functional groups. Preferred polyamines are the polyalkylene polyamines, for example, triethylenetetramine, tetraethylenepentamine, pentaethylenehexamine, hexamethyleneheptamine, and mixtures of two or more thereof. We have found in particular that the lower molecular weight polyalkylene amines, for example ethylenediamine and diethylenetriamine are relatively undesirable in that they are much less preferred than somewhat higher molecular weight polyamines, e.g., those having $\overline{M}_w$ at least as high as triethylenetetramine. Particularly preferred is a mixture of pentaethylenehexamine and hexamethyleneheptamine.

The reaction is preferably carried out by adding an aqueous solution of the prepolymer product to an aqueous solution of the polyamine. The order of addition is important, in that addition of the polyamine to the prepolymer product gives little or no polymerization. The prepolymer is preferably added slowly, and the viscosity measured continuously until the desired viscosity is reached.

The solution of the polymer produced generally has viscosity of from about 500 to about 5000 mPa/s, preferably from about 1000 to about 3000 mPa/s and a molecular weight ($\overline{M}_w$) of from about 7,500 to about 75,000, preferably from about 10,000 to about 60,000. It has been found suitable to utilize solutions of prepolymer and polyamine having a concentration of from about 35 percent to about 45 percent by weight of prepolymer or polyamine in the solution, preferably approximately 40 percent by weight. This results in the production of a polymer product having a concentration of from about 35 percent to about 45 percent by weight, preferably approximately 40 percent by weight. The temperature of the reaction mixture is preferably maintained in the range of from about 90° C. to 110° C., during addition of the prepolymer to the polyamine.

The invention is illustrated in the following examples.

EXAMPLES 1-5

A. Preparation of Prepolymer

Piperazine (86 g, one mole) is dissolved in 295 g of water in a one-liter glass flask, equipped with a heating mantle, stirrer, thermometer, reflux condenser, and dropping funnel. The mixture is heated to 60° C., and then 97.1 g of epichlorohydrin (1.05 moles) is added over a period of 1 hour, at a rate sufficient to maintain the temperature at about 100° C. When all the epichlorohydrin has been added, the mixture is stirred for a further period of 2 hours, during which it is maintained at 95° C. by applying heat, and the mixture is then cooled.

The concentration of the resulting prepolymer product in the aqueous solution is approximately 40 percent weight by weight (w/w) and the viscosity is about 80 mPa/s. The percentage conversion of organic chlorine to $Cl^{\ominus}$ is determined by potentiometric titration with AgNO$_3$, to provide a measure of the organically bonded chlorine content of the prepolymer product and is found to be about 7 percent w/w. The amount of free epichlorohydrin is also measured and found to be less than 100 ppm (weight).

The process is repeated using differing amounts of epichlorohydrin, so as to provide molar ratios of epichlorohydrin to piperazine of 1.1 (Example 2), 1.2 (Example 3), 1.3 (Example 4), 1.4 (Example 5) and 1.0 (Comparative Example 1) as shown in Table I.

TABLE I

| Sample No. | Amount of epi* (g) | Mole Ratio epi/pip** | % Chlorine Conversion |
|---|---|---|---|
| 1 | 97.1 | 1.05 | 90.5 |
| 2 | 101.0 | 1.1 | 87.1 |
| 3 | 111.0 | 1.2 | 81.5 |
| 4 | 120.0 | 1.3 | 76.4 |
| 5 | 129.5 | 1.4 | 71.0 |
| C1 | 92.5 | 1.0 | 99.0 |

*Epichlorohydrin
**Epichlorohydrin/piperazine

B. Preparation of Polymer Flocculants

Each of the aqueous solutions resulting from Samples 1 to 5 above is used for the preparation of a polymeric flocculant. In each case, the solution is reacted with a solution of 20 g of a polyalkylene polyamine in 30 g of water. The polyalkylene polyamine is a mixture of pentaethylenehexamine and hexaethyleneheptamine, with a $\overline{M}_w$ of about 260.

The mixed polyalkylene polyamine solution is heated in the same flask as used in Example 1, to a temperature of 90° C. The reaction mixture from the respective one of Examples 1 to 5 is then added gradually, and the viscosity measured regularly. The addition is stopped when the product has a viscosity of about 2000 mPa/s. The concentration of the product in water is about 40 percent w.w. The resulting solution is a light yellow to brown in color.

The weight ratio of the prepolymer to the polyalkylene polyamine is calculated, as is the mole ratio of the amount of epichlorohydrin used to form the prepolymer, to the total amine (including piperazine and polyethylene polyamine) in the product. The results are shown in Table II.

The efficacy of the resulting product as a flocculent is measured by adding 0.5 ml of a 1 percent solution of the product to 500 ml of an aqueous suspension of kaolin in water (0.5 w/w). The concentration of the polymer flocculant is thus 10 ppm. The mixture is thoroughly shaken, and observed in a 500-ml graduated cylinder, as the suspended kaolin is coagulated. The volume of supernatant liquid above the solid layer is used as a measure of the flocculating ability of the polymer. This volume is measured at regular intervals over a period of five minutes, and the results are also shown in Table II.

Table II also shows for the purposes of comparison the results obtained when the flocculating ability of the prepolymer of Example 3 was tested, and a standard commercially available flocculant, Purifloc C31 (Purifloc is a trademark) (Sample No. C2).

TABLE II

| Sample No. | Prepolymer Sample No. | wt ratio prepolymer/polyamine | mole ratio epi-total amine | conc. (ppm)[1] | Volume of supernatant liquid time (minutes) | | | | | | | Appearance water layer[2] |
|---|---|---|---|---|---|---|---|---|---|---|---|---|
| | | | | | 0.5 | 1.0 | 1.5 | 2.0 | 3.0 | 4.0 | 5.0 | |
| 1 | 1 | 17.8 | 1.01 | 10 | 410 | 330 | 145 | 120 | 95 | 90 | 85 | 1–2 |
| 2 | 2 | 6.8 | 0.99 | 10 | 375 | 200 | 135 | 110 | 90 | 80 | 75 | 0–1 |
| 3 | 3 | 3.9 | 1.00 | 10 | 370 | 195 | 130 | 110 | 90 | 85 | 80 | 0–1 |
| 4 | 4 | 3.6 | 1.00 | 10 | 360 | 205 | 135 | 120 | 100 | 90 | 80 | 1 |
| 5 | 5 | 2.3 | 1.03 | 15 | 370 | 210 | 135 | 120 | 100 | 85 | 80 | 1 |
| P3[3] | | | | 15 | 460 | 400 | 300 | 230 | 110 | 90 | 80 | 2–3 |
| C2 | | | | 10 | 375 | 220 | 150 | 110 | 110 | 95 | 90 | 0–1 |

[1] Concentration of flocculant in flocculation test
[2] 0 = water clear
0–1 = clear + some floating particles
1 = almost clear, some haziness
2 = fairly clear, more haziness than 1
3 = almost opaque
4 = completely opaque
[3] Prepolymer The product of comparative sample (C1) will not undergo polymerization with the polyalkylene polyamine. As can be seen from Table II, the flocculant polymers of Sample Nos. 1 to 5 have a flocculating ability which is comparable with, or better than that of Purifloc C31. The product of Sample No. 1, having an epichlorohydrin/piperazine ratio in the prepolymer of only 1.05 is slightly inferior. The flocculating ability of the prepolymer of Sample No. 3 is poor.

EXAMPLES 6 AND 7

A solution consisting of 163 g of the polyamine mixture used in Examples 1–5 and 244.5 g of water is heated to a temperature of 110° C., and the solution resulting from the prepolymer of Example 3 is added gradually, over a period of about three hours. The viscosity during this period at various weight ratios of prepolymer to polyamine is measured, as shown in Table III. Portions of the reaction mixture are removed at weight ratios of 3.75 (Example 6) and 4.00 (Example 7).

TABLE III

| Wt ratio prepolymer/polyamine | Viscosity mPa/s[1] |
|---|---|
| 3.2 | 570 |
| 3.64 | 1308 |
| 3.75 | 1887 (Ex 6) |
| 4.00 | 4600 (Ex 7) |

[1] Viscosity in millipascals is determined at approximately 25° C. using a Contraves Rheomat 1ST-FC Viscometer having a standard "C" spindle operating at a rate of 76 sec$^{-1}$.

EXAMPLES 8 AND 9

Examples 6 and 7 are repeated, except that an aqueous solution of 103 g of triethylenetetramine having a weight average molecular weight ($\overline{M}_w$) of 146 in 155 g of water is used, in place of the mixture of polyamines. The viscosity is measured as the polymerization progresses, and the results are shown in Table IV. Portions of the mixture are removed at weight ratios of prepolymer to polyamine of 7.9 (Example 8) and 8.5 (Example 9). The flocculation ability of the polymers of Examples 6 to 9 is measured as in Examples 5 to 5, and the results are shown in Table V.

TABLE IV

| Wt ratio prepolymer/tri-ethylenetetramine | Viscosity mPa/s[1] |
| --- | --- |
| 5.5 | 284 |
| 7.6 | 505 |
| 7.8 | 1355 |
| 7.9 | 1817 (Ex 8) |
| 8.5 | 4170 (Ex 9) |

[1]Viscosity in millipascals is determined at approximately 25° C. using a Contraves Rheomat 1ST-FC Viscometer having a standard "C" spindle operating at a rate of 76 sec$^{-1}$.

TABLE V

| | Volume of supernatant liquid[1] time (minutes) | | | | | | | Appearance[2] |
| --- | --- | --- | --- | --- | --- | --- | --- | --- |
| Ex | 0.5 | 1.0 | 1.5 | 2.0 | 3.0 | 4.0 | 5.0 | |
| 6 | 385 | 235 | 175 | 130 | 110 | 100 | 95 | 1 |
| 7 | 360 | 190 | 135 | 120 | 100 | 90 | 85 | 0–1 |
| 8 | 390 | 230 | 175 | 130 | 110 | 100 | 90 | 1 |
| 9 | 360 | 185 | 130 | 110 | 95 | 85 | 80 | 1 |

[1]Time in minutes for given volume of clear supernatant liquid to form.
[2]0 = water clear
0–1 = clear + some floating particles
1 = almost clear, some haziness
2 = fairly clear, more haziness than 1
3 = almost opaque
4 = completely opaque

What is claimed is:

1. A method of producing a nitrogen-containing water-soluble polymer, which method comprises (1) adding an epihalohydrin to a solution of piperazine, in an amount of more than one mole of epihalohydrin per mole of piperazine, in the substantial absence of strong base under conditions sufficient to produce a water-soluble prepolymer and (2) contacting the prepolymer with a polyfunctional amine in the substantial absence of strong base under conditions sufficient to produce a water-soluble nitrogen-containing polymer.

2. The method of claim 1 wherein the epihalohydrin is utilized in an amount of at least 1.1 moles per mole of piperazine.

3. The method of claim 1 wherein the epihalohydrin and the piperazine are utilized in the form of an aqueous solution.

4. The method of claim 3 wherein the concentration of epihalohydrin and piperazine in the aqueous solution are sufficient to produce a concentration of the prepolymer in the resulting aqueous solution before reaction with the polyfunctional amine of from about 35 percent to about 45 percent by weight.

5. The method of claim 1 wherein the reaction mixture is maintained at a temperature of from about 50° C. to about 110° C. during the addition.

6. The method of claim 5 wherein said temperature is in the range from about 90° C. to about 110° C.

7. The method of claim 1 wherein the reaction mixture is maintained at a temperature from about 90° C. to about 110° C. after the addition of the epihalohydrin to piperazine is complete, for a period of from about 1 to about 4 hours.

8. The method of claim 1 wherein the epihalohydrin is epichlorohydrin.

9. The method of claim 1 wherein the reaction of the prepolymer with the polyamine is carried out by adding an aqueous solution of the prepolymer to an aqueous solution of the polyamine.

10. The method of claim 8 wherein the concentration of the prepolymer and the polyamine are such as to produce in the resultant mixture a polymer product having a concentration of from about 35 percent to about 45 percent by weight.

11. The method of claim 8 wherein the amount of the prepolymer added to the polyamine is such that the viscosity of the resulting product is from about 500 to about 5,000 mPas.

12. The method of claim 1 wherein the polyamine is triethylenetetramine, tetraethylenepentamine, pentaethylenehexamine, hexamethyleneheptamine, or a mixture of two or more thereof.

13. The method of claim 1 wherein the reaction of the prepolymer with the polyamine is carried out at a temperature of from about 90° C. to about 110° C.

14. A nitrogen-containing, water-soluble polymer, prepared by the reaction of an epihalohydrin with piperazine in the substantial absence of strong base, to form a prepolymer, and the subsequent reaction of the prepolymer with a polyamine in the substantial absence of strong base, to form the water-soluble, nitrogen-containing polymer.

15. A flocculant composition comprising the polymer of claim 14.

16. A method of causing flocculation of an aqueous liquid, which method comprises adding to the liquid an amount of the water-soluble, nitrogen-containing polymer of claim 14.

* * * * *